US010849926B2

(12) United States Patent
Inokuchi et al.

(10) Patent No.: US 10,849,926 B2
(45) Date of Patent: Dec. 1, 2020

(54) GM3-PROMOTED INFLAMMATION INHIBITOR AND INFLAMMATORY CYTOKINE PRODUCTION INHIBITOR

(71) Applicant: THE NOGUCHI INSTITUTE, Tokyo (JP)

(72) Inventors: Jin-Ichi Inokuchi, Sendai (JP); Hirotaka Kanoh, Sendai (JP); Sandro Sonnino, Milan (IT)

(73) Assignee: THE NOGUCHI INSTITUTE, Tokyo (JP)

( * ) Notice: Subject to any disclaimer, the term of this patent is extended or adjusted under 35 U.S.C. 154(b) by 0 days.

(21) Appl. No.: 15/775,189

(22) PCT Filed: Nov. 29, 2016

(86) PCT No.: PCT/JP2016/085323
§ 371 (c)(1),
(2) Date: May 10, 2018

(87) PCT Pub. No.: WO2017/094705
PCT Pub. Date: Jun. 8, 2017

(65) Prior Publication Data
US 2018/0353535 A1 Dec. 13, 2018

(30) Foreign Application Priority Data

Nov. 30, 2015 (JP) ................. 2015-232564
Jun. 8, 2016 (JP) ................. 2016-114188

(51) Int. Cl.
| A61K 31/739 | (2006.01) |
|---|---|
| A61P 37/06 | (2006.01) |
| A61P 29/00 | (2006.01) |
| A61K 45/00 | (2006.01) |
| A61K 31/00 | (2006.01) |

(52) U.S. Cl.
CPC ............ *A61K 31/739* (2013.01); *A61K 31/00* (2013.01); *A61K 45/00* (2013.01); *A61P 29/00* (2018.01); *A61P 37/06* (2018.01)

(58) Field of Classification Search
CPC ......... A61K 31/739; A61P 37/06; A61P 29/00
See application file for complete search history.

(56) References Cited

U.S. PATENT DOCUMENTS

| 2007/0173480 A1 | 7/2007 | Clandinin et al. |
| 2008/0108684 A1 | 5/2008 | Matsumoto et al. |
| 2011/0262441 A1 | 10/2011 | Inokuchi et al. |

FOREIGN PATENT DOCUMENTS

| JP | 2005-187341 A | 7/2005 |
| JP | 2007-131550 A | 5/2007 |
| JP | 2008-214241 A | 9/2008 |
| KR | 10-2013-0122110 A | 11/2013 |
| WO | 2007/004613 A1 | 1/2007 |
| WO | 2010/050584 A1 | 5/2010 |
| WO | 2011/133918 A1 | 10/2011 |
| WO | 2016/072364 A1 | 5/2016 |

OTHER PUBLICATIONS certified copy of the Japan 2016-114188, published Jun. 8, 2017 (Year: 2017).*
Schnabl et al., Journal of Pediatric Gastroenterology and Nutrition, 2009, 49, p. 382-392. (Year: 2009).*
Prokazova et al., Biochemistry (Moscow), 2009, 74(3), pp. 235-249. (Year: 2009).*
Tanabe et al., Biochemical and Biophysical Research Communications, 2009, 379, p. 547-552. (Year: 2009).*
Extended Search Report dated May 29, 2019, issued in counterpart EP Application No. 16870642.2 (10 pages).
"Ganglioside—Wikipedia", Mar. 1, 2015, URL:https://en.wikipedia.org/w/index.php?title=Ganglioside&oldid=650161478; Cited in Extended EP Search Report dated May 29, 2019.
Tsukuda, Yukinori et al., "Ganglioside GM3 Has an Essential Role in the Pathogenesis and Progression of Rheumatoid Arthritis", PLOS One, Jun. 29, 2012, vol. 7, No. 6, pp. 1-9; Cited in Extended EP Search Report dated May 29, 2019.
Shen et al., "Inhibition of TLR Activation and Up-Regulation of IL-1R-Associated Kinase-M Expression by Exogenous Gangliosides", The Journal of Immunology, 2008, 180, pp. 4425-4432. Cited in Specification. (8 pages).
Jou et al., "Gangliosides Trigger Inflammatory Responses via TLR4 in Brain Glia", American Journal of Pathology, May 2006, No. 5, vol. 168. Cited in Specification. (12 pages).
Senn et al., "Gangliosides in normal human serum Concentration, pattern and transport by lipoproteins", Eur. J. Biochem, Feb. 1989, vol. 181, pp. 657-662. Cited in Specification. (6 pages).
Tagami et al., Ganglioside GM3 Participates in the pathological conditions of insulin resistance, The Journal of Biological Chemistry, Feb. 1, 2002, vol. 277, No. 5, pp. 3085-3092. Cited in Specification & ISR. (9 pages).
Kabayama et al., "Dissociation of the insulin receptor and caveolin-1 complex by ganglioside GM3 in the state of insulin resistance", The National Academy of Sciences of the USA, Aug. 21, 2007, vol. 104, No. 34, pp. 13678-13683. Cited in Specification. (9 pages).

(Continued)

*Primary Examiner* — Jonathan S Lau
(74) *Attorney, Agent, or Firm* — Westerman, Hattori, Daniels & Adrian, LLP

(57) ABSTRACT

The agent for inhibiting inflammation promoted by GM3 of the present invention comprises a substance that inhibits inflammation promoted by GM3 as an active ingredient. The substance which inhibits inflammation promoted by GM3 is preferably a ganglioside having 2 or more of sialic acids. The ganglioside having 2 or more of sialic acids is at least one kind of ganglioside selected from the group consisting of GD1c, GD1a, GT1a, GD3, GD2, GD1b, GT1b, GQ1b, GT3, GT2, GT1c, GQ1c, and GP1c. Further, the substance which inhibits inflammation promoted by GM3 has a structure represented by the following formula (1): [In the formula (1), $R^1$ represents a glycan constituting ganglioside GM3, $R^2$—C(=O)— represents a fatty acid residue having 18 or less of carbon atoms, or an unsaturated fatty acid residue having 20 or more of carbon atoms.]

4 Claims, 14 Drawing Sheets

(56) References Cited

OTHER PUBLICATIONS

Nagafuku et al., "Control of homeostatic and pathogenic balance in adipose tissue by ganglioside GM3", Glycobiology, 2015, vol. 25, No. 3, pp. 303-318. w/English Abstract, Cited in Specification. (16 pages).

Veillon et al., "Identification of Ganglioside GM3 Molecular Species in Human Serum Associated with Risk Factors of Metabolic Syndrome", Jun. 23, 2015. w/English Abstract, Cited in Specification. (15 pages).

Wang et al., Gangliosdie GD1a suppresses LPS-induced pro-inflammatory cytokines in RAW264.7 macrophages by reducing MAPKs and NF-kB signaling pathways through TLR4, International Immunopharmacology, PLOS One, Jun. 2015, vol. 28, No. 1, pp. 136-145. w/English Abstract. Cited in ISR. (10 pages).

Okuyama et al., "The involvement of glycans in the regulation of allergic immune responses", w/English Translation. Cited in ISR. (14 pages).

Kabayama et al., "TNFα-induced insulin resistance in adipocytes as a membrane microdomain disorder: involvement of ganglioside GM3", Glycobiology, 2005, vol. 15, No. 1, pp. 21-29. w/English Translation. Cited in ISR. (9 pages).

Miklavcic et al., "Increased catabolism and decreased unsaturation of ganglioside in patients with inflammatory bowel disease", World Journal of Gastroenterology, Sep., 21 2015, vol. 21, No. 35, pp. 10080-10090. w/English Abstract. Cited in ISR. (12 pages).

Tatamizawa et al., "Gangliosides of Bovine Buttermilk", The Journal of Biological Chemistry, 1986, vol. 261, No. 12, pp. 5625-5630. Cited in ISR. (6 pages).

International Search Report dated Jan. 17, 2017 issued in Counterpart of International Application No. PCT/JP2016/085323 (3 pages).

Office Action dated Apr. 7, 2020, issued in counterpart JP Application No. 2017-553864, with English translation (12 pages).

* cited by examiner

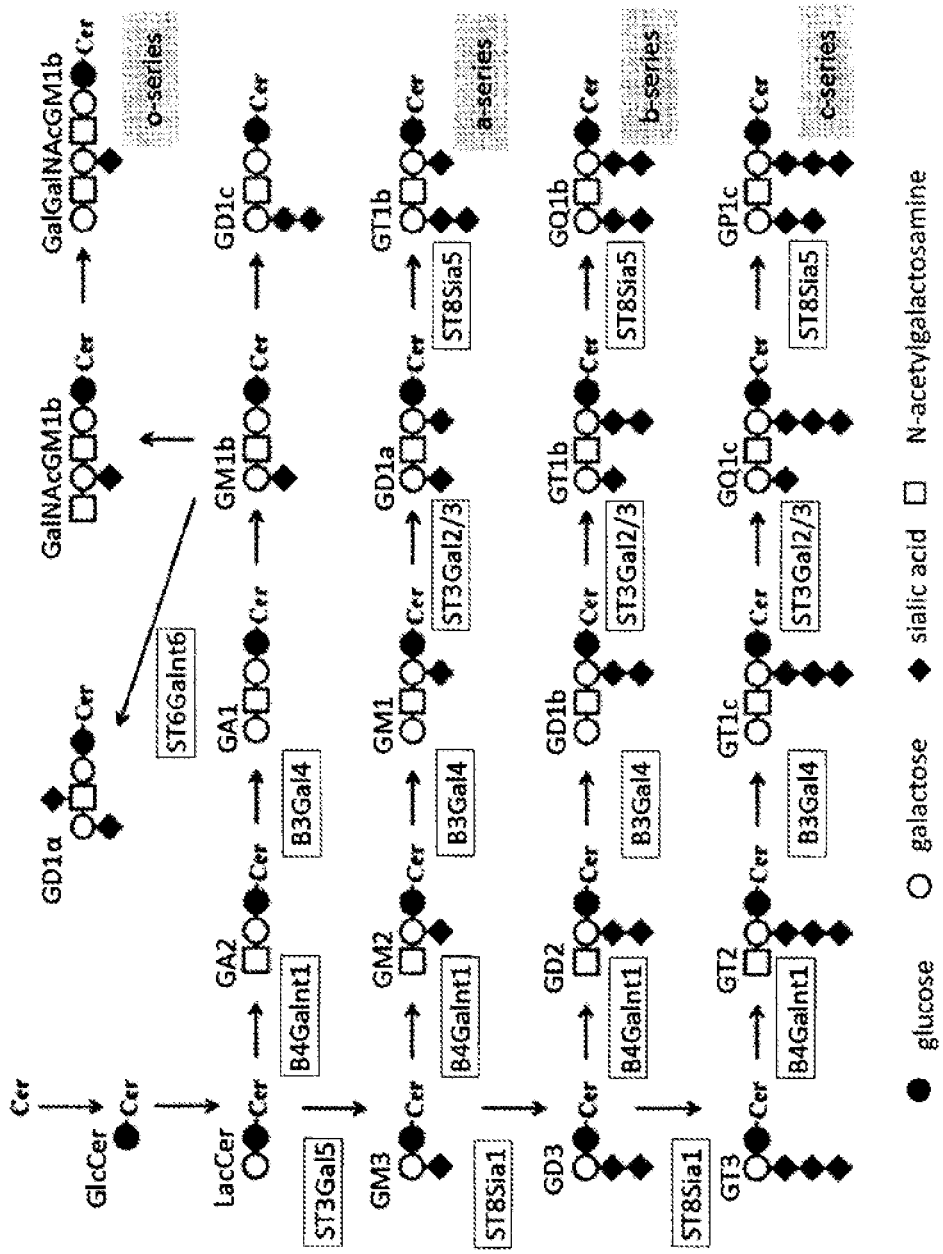
[Fig. 1]

[Fig. 2]
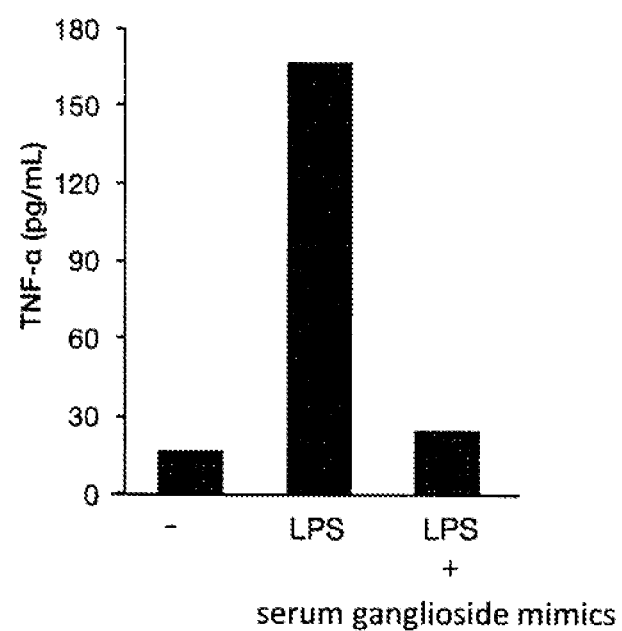

[Fig. 3]
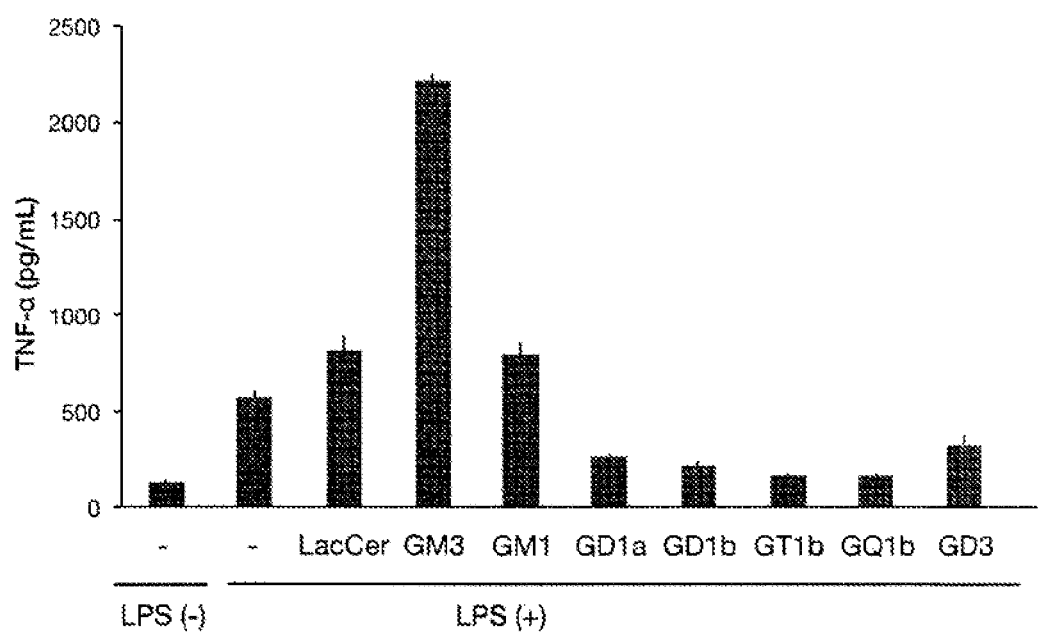

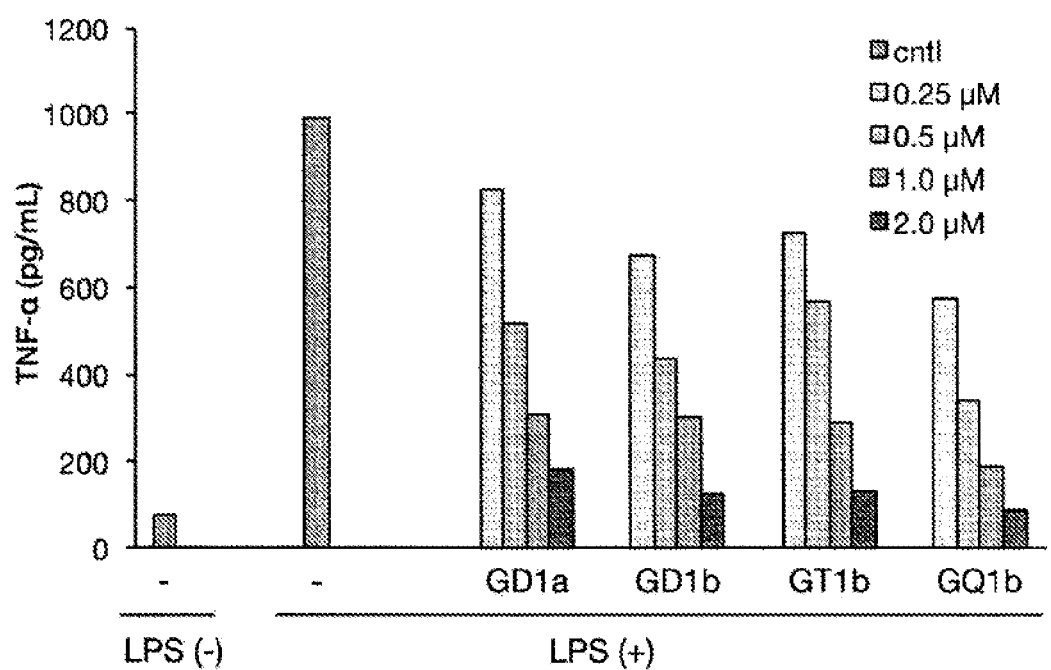
[Fig. 4]

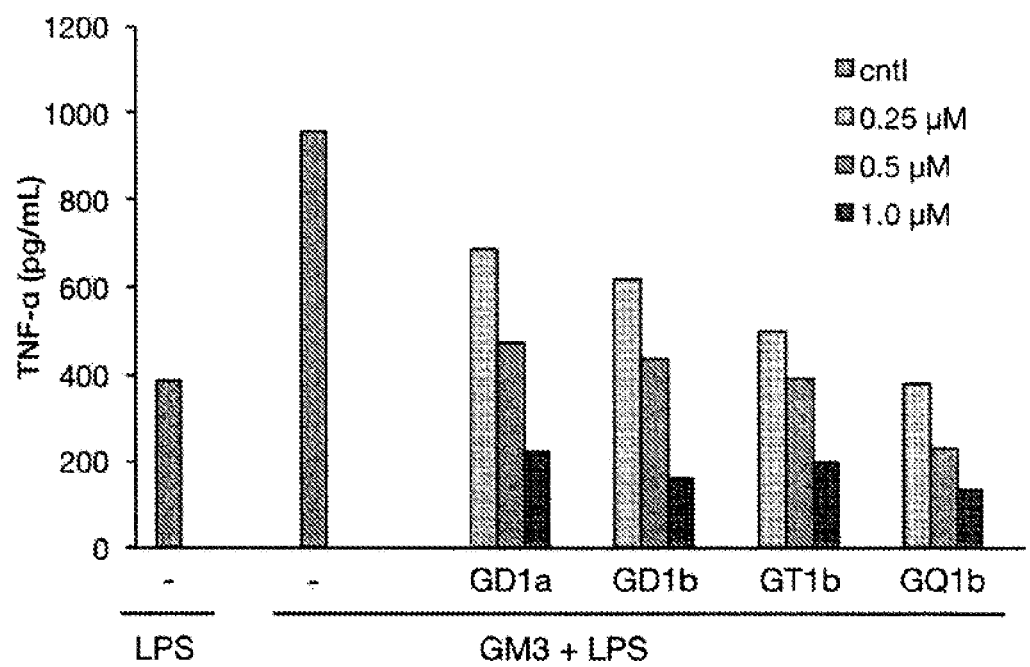
[Fig. 5]

[Fig. 6]
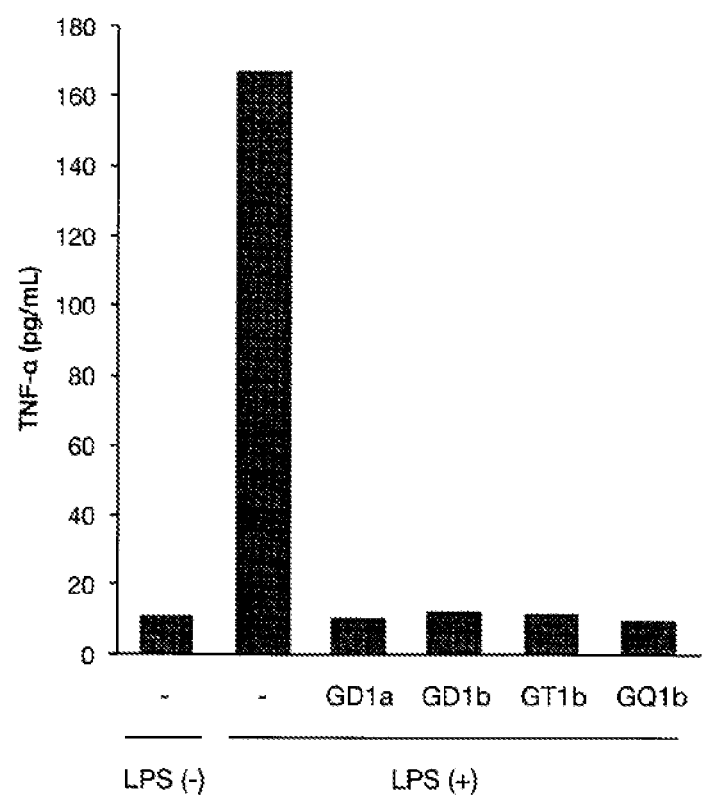

[Fig. 7]
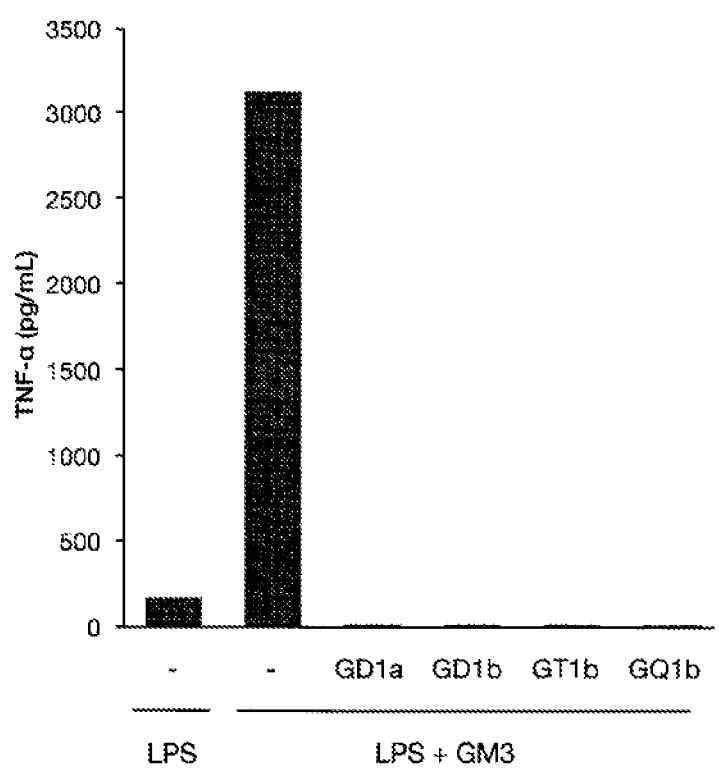

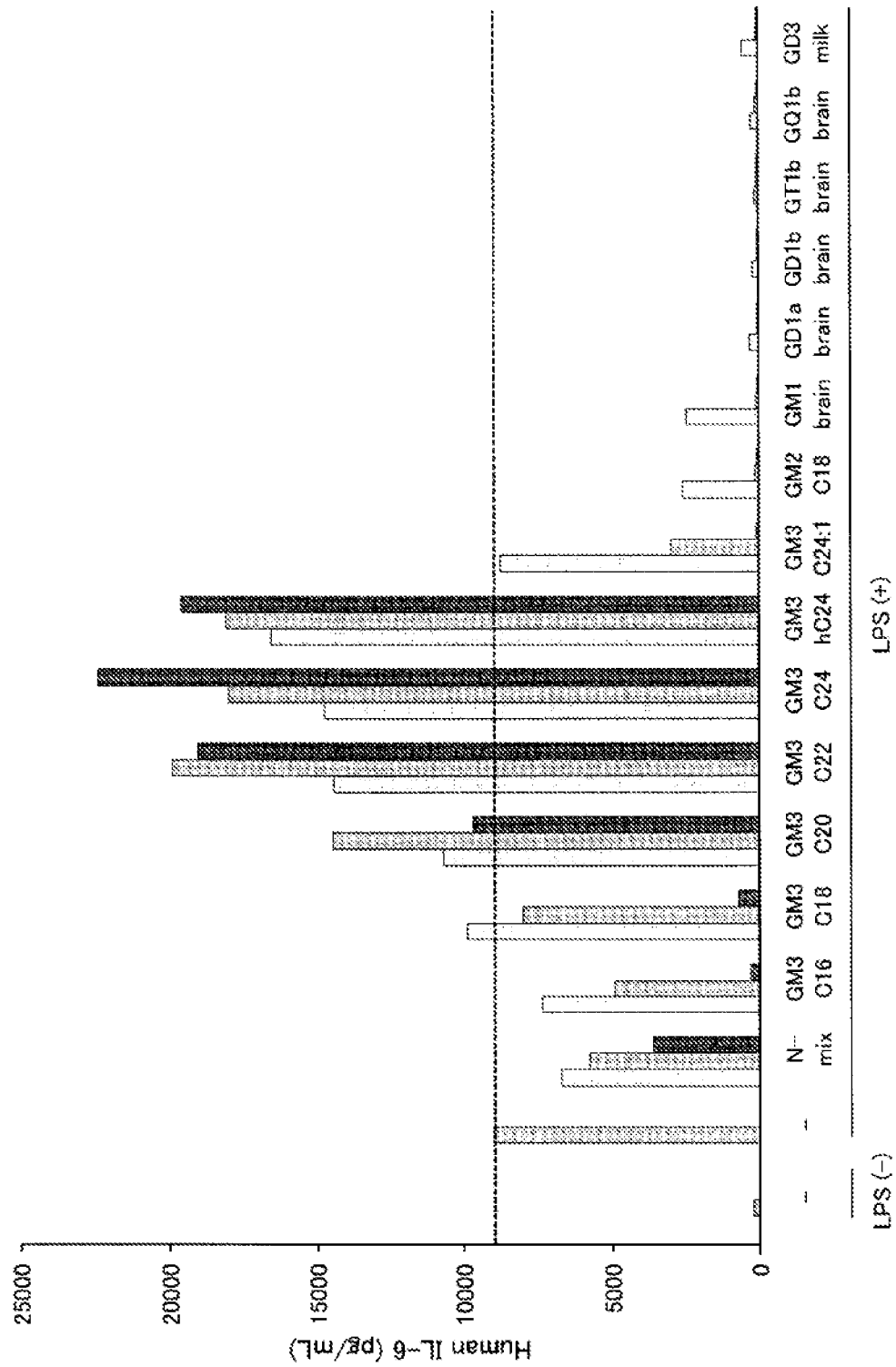
[Fig. 8]

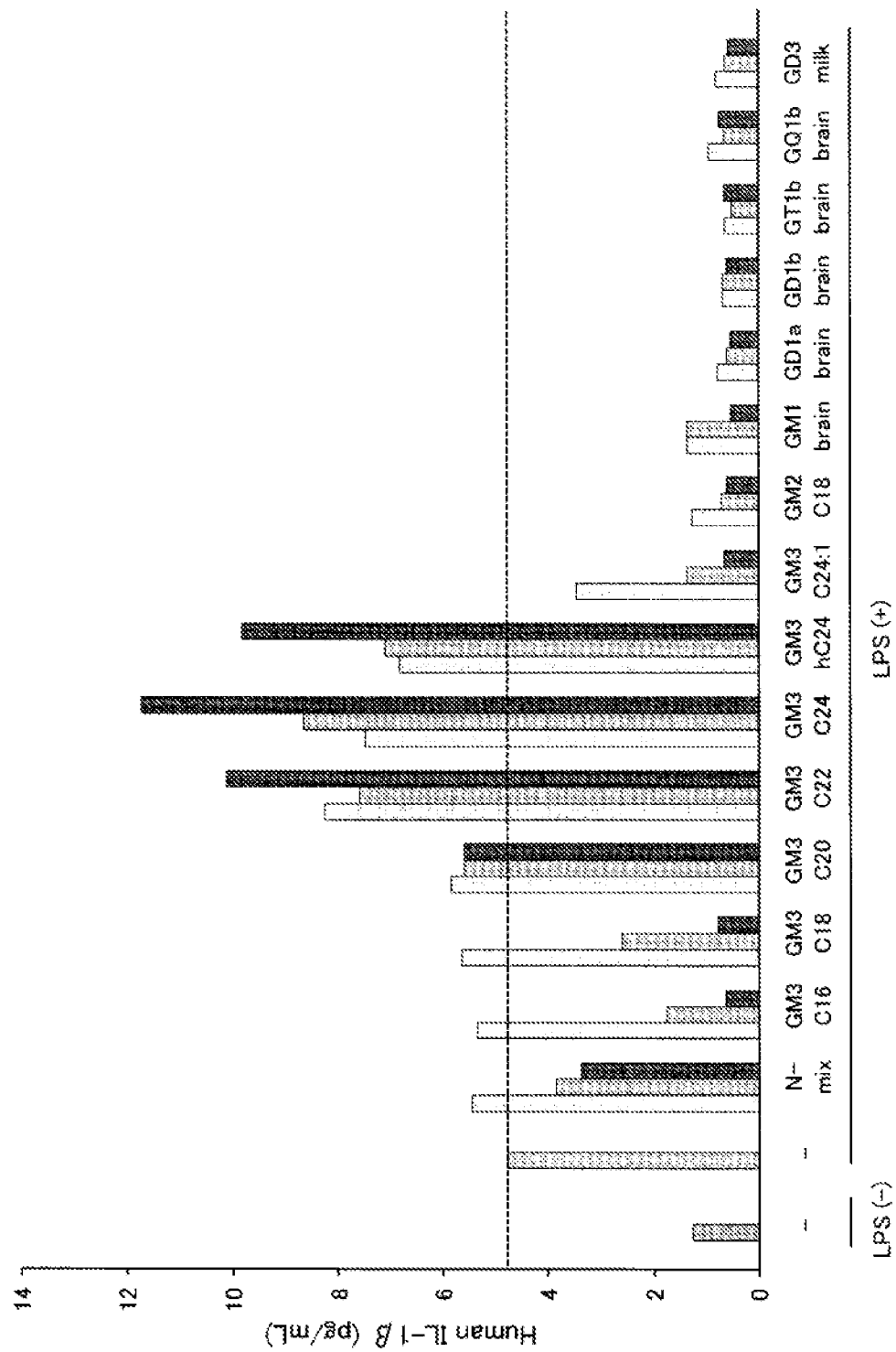
[Fig. 9]

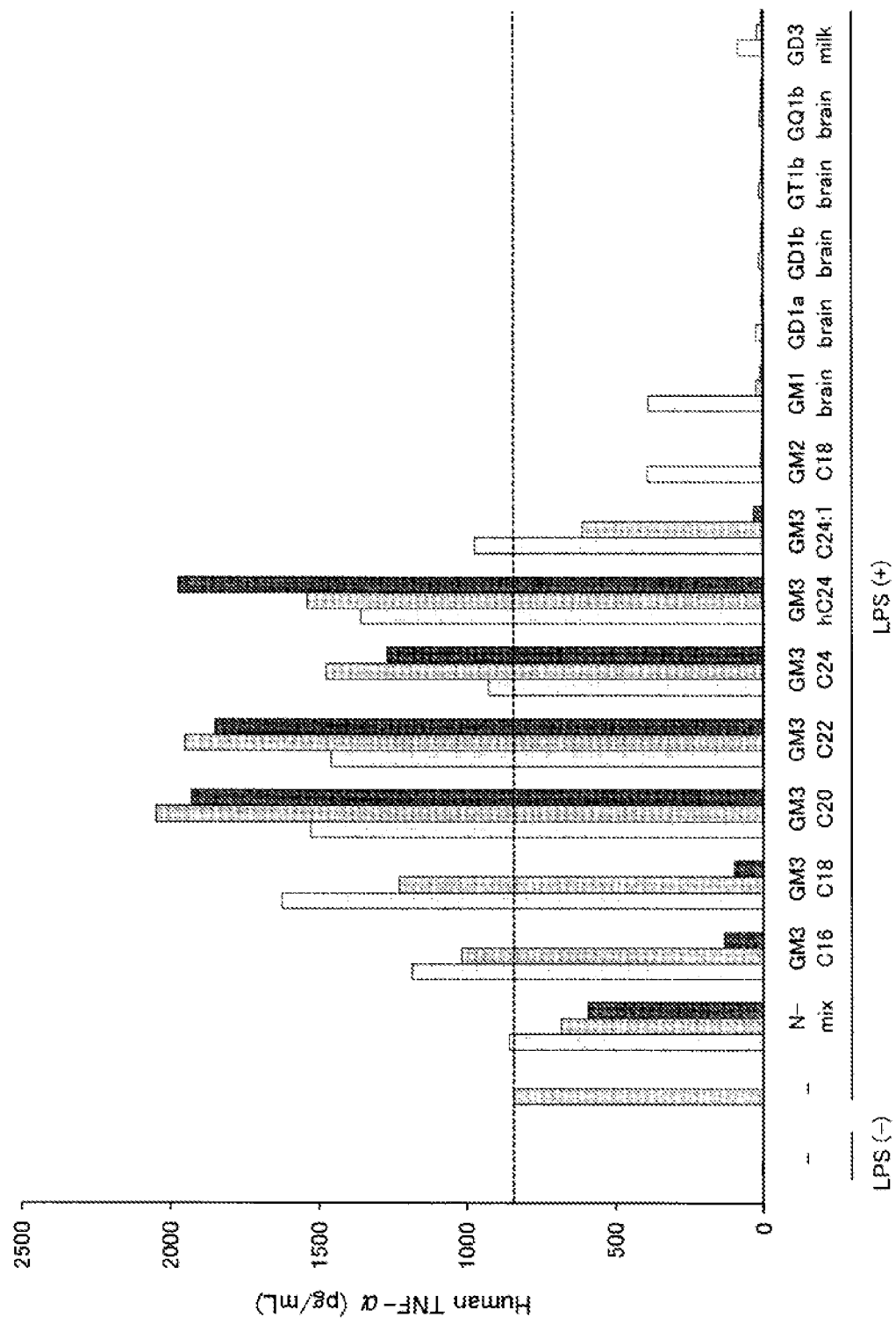
[Fig. 10]

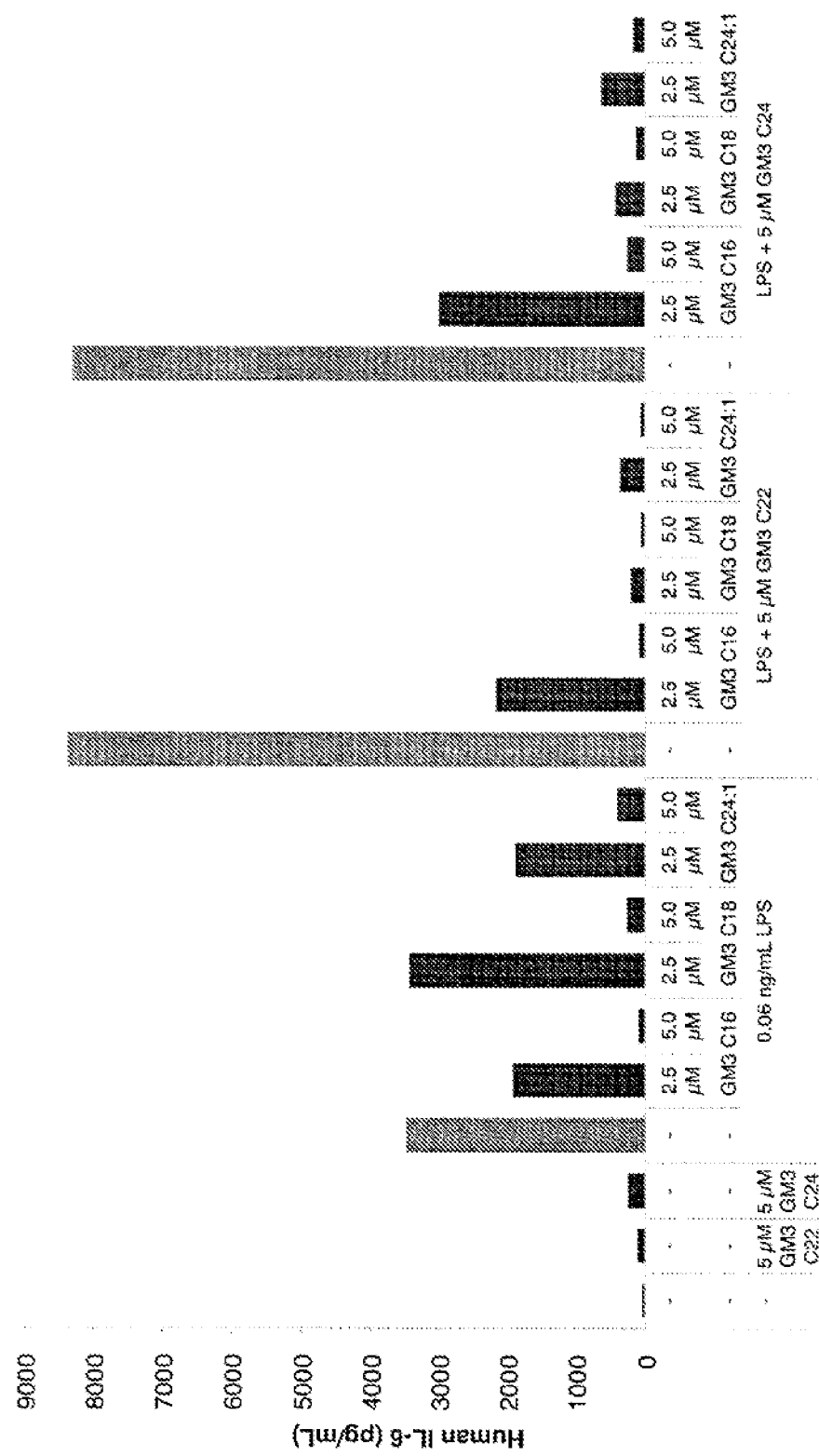
[Fig. 11]

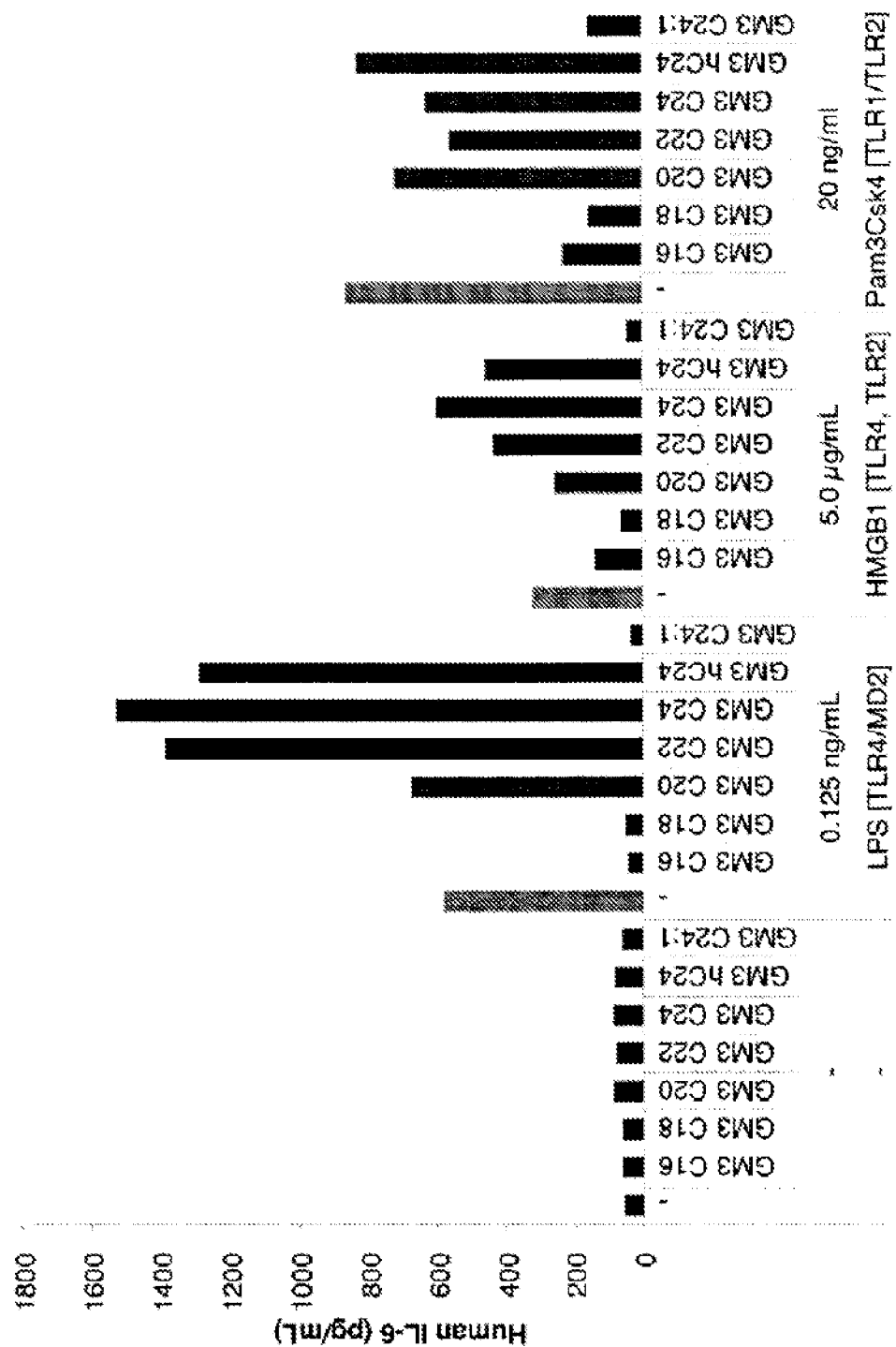
[Fig. 12A]

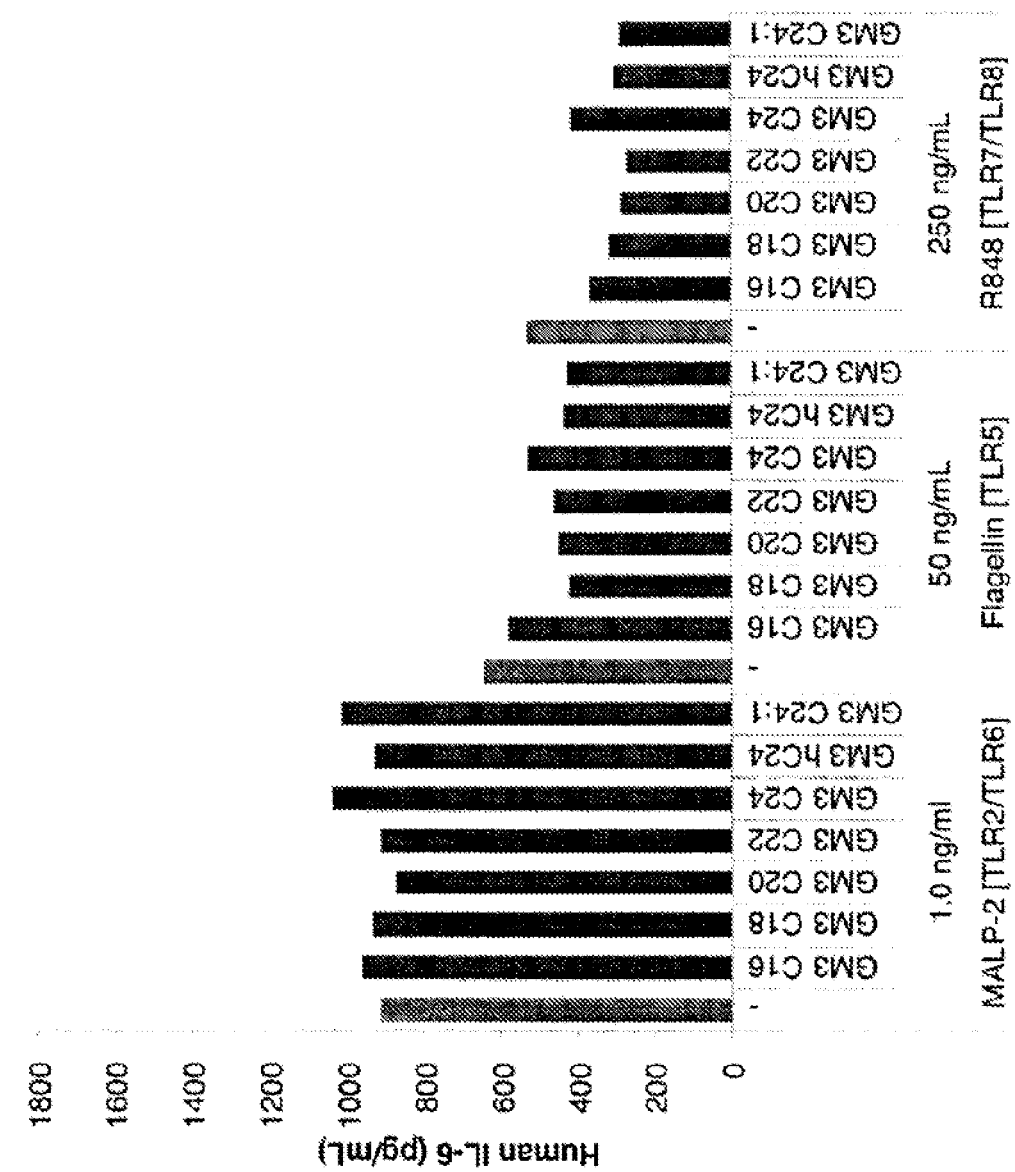
[Fig. 12B]

[Fig. 13]
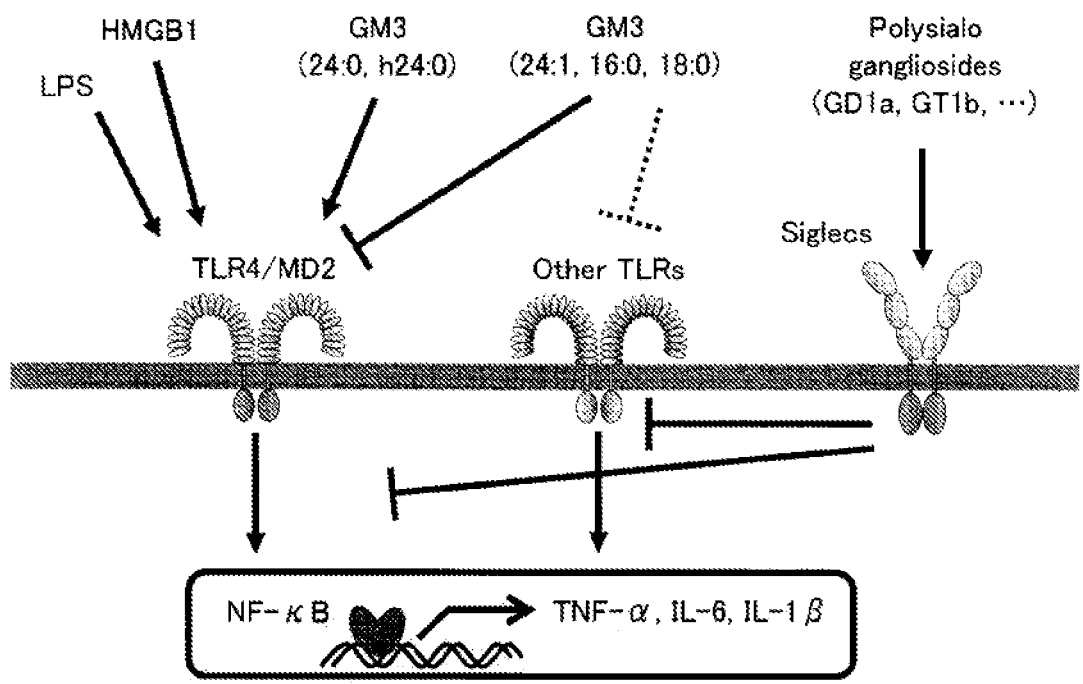

ved by the inventors' previous
GM3-PROMOTED INFLAMMATION INHIBITOR AND INFLAMMATORY CYTOKINE PRODUCTION INHIBITOR

TECHNICAL FIELD

The present invention relates to an agent for inhibiting inflammation promoted by GM3 and an agent for inhibiting production of an inflammatory cytokine.

BACKGROUND ART

It has been so far shown that inflammatory cytokines are secreted from activated tissue macrophages in mice fed high-fat diets and obese model mice by genetic modification, thereby acting on neighboring adipocytes and inducing expression of GM3 which is responsible for insulin resistance. On the other hand, it is clear that, in GM3 synthase knockout mice in which the production of GM3 does not occur, not only the insulin resistance is improved, but also the production of inflammatory cytokines from macrophages is decreased, and the mice are released from chronic inflammatory conditions. This strongly suggests that GM3 is the main endogenous ligand which induces chronic inflammation during obesity.

Further, so many molecular species exist in gangliosides including GM3 due to the diversity of ceramide and glycan structures, and many of them are expressed in the immune system. These findings suggest that not only GM3 but also various ganglioside molecular species are involved in a molecular mechanism of the inducing and inhibiting of chronic inflammation during obesity. In fact, studies using various ganglioside molecular species have been attempted in numerous cell types. However, there are few unified findings on the activation and inhibitory action on inflammatory response by gangliosides including GM3. The reason for this is considered to be that the previous reports are a collection of findings obtained by experiments using gangliosides without the specification of molecular species and the appropriate selection of target cell.

For example, W. Shen et al. shows that several gangliosides (GM1, GD1a, and GD1b) inhibited the activation of Toll-like receptor (TLR) by various pathogen-associated molecular patterns (PAMPs), and GM3 exhibited neither the inhibition nor the activation effects (Non-Patent Literature 1).

However, these results were obtained by the experiments using unfractionated human peripheral blood mononuclear cells, and, therefore, it is not clear whether these effects are due to the contribution of innate immune cells or lymphoid cells. Accordingly, it is difficult to accurately define the interaction of ganglioside with the immune system and the degree of influence thereof.

Further, I. Jou et al. have shown the results completely opposite from Non-Patent Literature 1 (Non-Patent Literature 2). This report shows that, in the rat's central nervous system-derived microglia, number of gangliosides (GM1, GD1a, GD1b, GT1b, GQ1b, and a mixture thereof) activated TLR4.

However, the experimental system used in this report is a flow cytometric analysis to measure the internalization of TLR4, demonstrating not direct activation of TLR4 signaling. Regarding some gangliosides, an increase in mRNA of tumor necrosis factor-alpha (TNF-α) produced by activation of TLR4 is demonstrated. However, this report is consistently based on the results obtained by non-quantitative determination of a weak increase using RT-PCR. There is no confirmed data showing the secretion of TNF-α which actually proves the activation of microglia.

Further, H J. Senn et al. shows that there is a sufficient amount of ganglioside in the serum of a mammal to exert its physiological activity (Non-Patent Literature 3). The report of I. Jou et al. does not accurately reflect the physiological activity of each of the gangliosides because various gangliosides are added in the presence of 5% or more of fetal bovine-derived serum. Thus, this is considered to be the result including the background produced by the serum-derived gangliosides. Therefore, it is questionable to regard these results as accurate and physiological activity of gangliosides under physiological concentration. Therefore, these reasons are also able to explain the contradictory results.

As described above, many reports show contradictory results on the bioactivity of gangliosides at present.

Further, Patent Literature 1 discloses a prostaglandin $E_2$ production inhibitor, which contains a sphingolipid such as ganglioside. Prostaglandin $E_2$ is an inflammatory factor, which causes fever and enhances vascular permeability. However, the literature does not describe specific molecular species of ganglioside which exhibited an inhibitory action on prostaglangin $E_2$ producing inflammation.

PRIOR ART REFERENCES

Patent Documents

Patent Document 1: JP 2005-187341 A

Non Patent Literature

Non Patent Document 1: Shen, W. et al., J Immunol., 180:4425-32, 2008
Non Patent Document 2: Jou, I. et al., Am J Pathol., 168:1619-30, 2006
Non Patent Document 3: Senn, H J. et al., Eur J Biochem., 181: 657-62, 1989

SUMMARY OF INVENTION

Problems to be Solved by the Invention

The present invention has been made in view of the above background art, and an object of the present invention is to provide a novel anti-inflammatory agent containing a substance which has an inhibitory action on inflammation as an active ingredient.

Means to Solve the Problems

The inventors of the present invention have conducted intensive studies to solve the above-mentioned problems. As a result, they have constructed a system which accurately measures the activity of ganglioside present in the serum and revealed the strong inflammation-inducing effect of GM3 for the first time. Further, they have found a strong inhibitory action of serum ganglioside molecular species other than GM3 on inflammation.

Furthermore, focusing on the mechanism of onset of chronic inflammatory conditions via ganglioside during obesity, which has been revealed by the inventors' previous work (Tagami S. et al., J. Biol. Chem., 277: 3085-92, 2002; Kabayama K. et al., Proc. Natl. Acad. Sci., 104: 13678-83, 2007; Nagafuku M. et al., Glycobiology, 25: 303-318, 2015; Veillon L. et al., Plos One, 2015), the mechanisms of induction and inhibition of chronic inflammation by various gangliosides including GM3 in macrophages have been verified.

As a result, it has been first found out that GM3 promotes "an inflammatory reaction induced by activation of macrophages with lipopolysaccharides (LPSs)". Then, it has also been found out that GD3, GD1a, GD1b, GT1b, and GQ1b having such specific glycan structures have an anti-inflammatory activity to antagonize "GM3-dependent macrophage activation".

Further, it has been surprisingly found out that GM3 having a specific structure with respect to the fatty acid in the ceramide moiety has an anti-inflammatory activity to antagonize the inflammatory reaction induced by LPS in macrophages, thereby completing the present invention.

That is, the present invention is as follows:

[1] An agent for inhibiting inflammation promoted by GM3, comprising a substance which inhibits inflammation promoted by GM3 as an active ingredient.

[2] The agent for inhibiting inflammation promoted by GM3 according to [1], wherein the substance which inhibits inflammation promoted by GM3 is a ganglioside having 2 or more of sialic acids.

[3] The agent for inhibiting inflammation promoted by GM3 according to [1], wherein the substance which inhibits inflammation promoted by GM3 has a structure represented by the following formula (1):

[Chemical Formula 1]

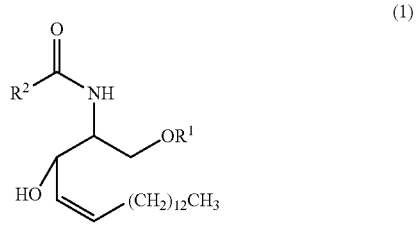

(1)

[In the formula (1), $R^1$ represents a glycan constituting ganglioside GM3, $R^2$—C(=O)— represents a fatty acid residue having 18 or less of carbon atoms, or an unsaturated fatty acid residue having 20 or more of carbon atoms.]

[4] The agent for inhibiting inflammation promoted by GM3 according to [2], wherein the ganglioside having 2 or more of sialic acids is at least one kind of ganglioside selected from the group consisting of GD1c, GD1a, GT1a, GD3, GD2, GD1b, GT1b, GQ1b, GT3, GT2, GT1c, GQ1c, and GP1c.

[5] An agent for inhibiting production of an inflammatory cytokine, comprising a substance which inhibits the production of an inflammatory cytokine promoted by GM3 as an active ingredient.

[6] The agent for inhibiting production of an inflammatory cytokine according to [5], wherein the substance which inhibits the production of an inflammatory cytokine promoted by GM3 is a ganglioside having 2 or more of sialic acids.

[7] The agent for inhibiting production of an inflammatory cytokine according to [6], wherein the ganglioside having 2 or more of sialic acids is at least one kind of ganglioside selected from the group consisting of GD1c, GD1a, GT1a, GD3, GD2, GD1b, GT1b, GQ1b, GT3, GT2, GT1c, GQ1c, and GP1c.

[8] The agent for inhibiting production of an inflammatory cytokine according to [5], wherein the substance which inhibits the production of an inflammatory cytokine promoted by GM3 has a structure represented by the following formula (1):

[Chemical Formula 2]

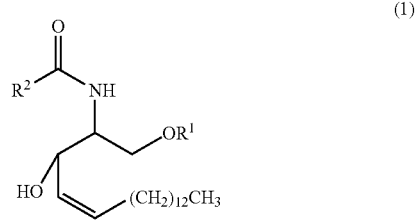

(1)

[In the formula (1), $R^1$ represents a glycan constituting ganglioside GM3, $R^2$—C(=O)— represents a fatty acid residue having 18 or less of carbon atoms, or an unsaturated fatty acid residue having 20 or more of carbon atoms.]

Effects of Invention

The agent for inhibiting inflammation promoted by GM3 and the agent for inhibiting production of an inflammatory cytokine of the present invention solve the above problems, have an effect of inhibiting inflammation promoted by GM3, and have an effect of improving chronic inflammatory diseases and systemic inflammatory conditions.

Further, the agent for inhibiting inflammation promoted by GM3 and the agent for inhibiting production of an inflammatory cytokine of the present invention are safe for humans and the like and have the effect of reducing burden and side effects to subjects.

Further, GM3 is a ganglioside whose expression is increased during obesity, and the agent for inhibiting inflammation promoted by GM3 and the agent for inhibiting production of an inflammatory cytokine of the present invention have an effect of inhibiting chronic inflammation during obesity.

BRIEF DESCRIPTION OF DRAWINGS

FIG. 1 is a view that illustrates a biosynthetic pathway of ganglioside molecular species in mammals.

FIG. 2 is a graph showing an inhibitory activity of serum ganglioside mimic on LPS-dependent TNF-α production.

FIG. 3 is a graph showing an enhancing effect of TNF-α production cooperatively with GM3 and LPS and an inhibitory activity of other gangliosides (GD1a, GD1b, GT1b, GQ1b, and GD3).

FIG. 4 is a graph showing a concentration-dependent inhibitory action of inhibitory gangliosides on LPS-dependent TNF-α production.

FIG. 5 is a graph showing a concentration-dependent inhibitory action of inhibitory gangliosides on "TNF-α production cooperatively with LPS and GM3".

FIG. 6 is a graph showing an inhibitory action of inhibitory gangliosides on LPS-dependent TNF-α production in bone marrow-derived macrophages.

FIG. 7 is a graph showing an inhibitory action of inhibitory gangliosides on "TNF-α production cooperatively with LPS and GM3 in bone marrow-derived macrophages".

FIG. 8 is a graph showing an enhancing or inhibitory action of ganglioside molecular species on LPS-dependent human IL-6 production.

FIG. 9 is a graph showing an enhancing or inhibitory action of ganglioside molecular species on LPS-dependent human IL-1β production.

FIG. 10 is a graph showing an enhancing or inhibitory action of ganglioside molecular species on LPS-dependent human TNF-α production.

FIG. 11 is a graph showing an inhibitory action of ganglioside molecular species on GM3- and/or LPS-dependent human IL-6 production.

FIG. 12A is a graph showing a Toll-like receptor selective enhancing and inhibitory action of GM3 on inflammation.

FIG. 12B is a graph showing a Toll-like receptor selective enhancing and inhibitory action of GM3 on inflammation.

FIG. 13 is a schematic diagram that illustrates a mechanism in which LPS-dependent inflammation is expected to be enhanced or inhibited by ganglioside molecular species.

EMBODIMENTS TO CARRY OUT THE INVENTION

Hereinafter, the present invention will be described. However, the present invention is not limited to the following specific embodiments, and can be arbitrarily modified within the scope of the present invention.

<Agent for Inhibiting Inflammation Promoted by GM3>

The agent for inhibiting inflammation promoted by GM3 of the present invention comprises a substance that inhibits inflammation promoted by GM3 as an active ingredient. Since a strong inflammation-inducing action by GM3 has not been revealed so far, "an agent for inhibiting inflammation promoted by GM3" has been first found out in the present invention.

In the present specification, the term "agent for inhibiting inflammation promoted by GM3" refers to an inhibitor having an action of inhibiting "GM3-dependent inflammation promoted/induced by GM3".

Generally, the term "ganglioside" refers to a glycosphingolipid in which at least one sialic acid is bonded to a glycan.

In the present specification, the term "GM3" refers to "ganglioside GM3", and in the case of humans, it refers to "ganglioside GM3" in which the glycan of glycosphingolipid is the following structure.

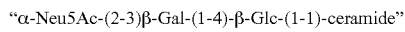

"α-Neu5Ac-(2-3)β-Gal-(1-4)-β-Glc-(1-1)-ceramide"

Here, "α-Neu5Ac" is α-N-acetyl-neuraminic acid, "β-Gal" is β-galactose, and "β-Glc" is β-glucose.

Further, the inflammation is promoted by "GM3 in which the fatty acid residue is a saturated fatty acid having 20 or more of carbon atoms", and thus the above "inflammation promoted by GM3" is preferably "inflammation promoted by GM3 in which the fatty acid residue is a saturated fatty acid having 20 or more of carbon atoms" (GM3 which promotes inflammation may be specified as GM3 in which the fatty acid residue is a saturated fatty acid residue having 20 or more of carbon atoms).

Further, inflammation is promoted by "GM3 which may have an OH group as a substituent and in which the fatty acid residue is a saturated fatty acid having 24 carbon atoms", and thus the above "inflammation promoted by GM3" is more preferably "inflammation promoted by GM3 which may have an OH group as a substituent and in which the fatty acid residue is a saturated fatty acid having 24 carbon atoms" (GM3 which promotes inflammation may be specified as GM3 which may have an OH group as a substituent and in which the fatty acid residue is a saturated fatty acid having 24 carbon atoms).

In this example, it has been first revealed that GM3 molecular species include GM3 which enhances inflammation (GM3 in which the fatty acid is a saturated fatty acid having 20 or more of carbon atoms) and GM3 which inhibits inflammation (GM3 in which the fatty acid is a fatty acid having 18 or less of carbon atoms, or the fatty acid is an unsaturated fatty acid having 20 or more of carbon atoms (particularly an unsaturated fatty acid having 24 carbon atoms), and one double bond is included in the hydrocarbon group of the unsaturated fatty acid).

The substance which inhibits inflammation promoted by GM3, i.e., an active ingredient of the agent for inhibiting inflammation promoted by GM3 of the present invention, may consist of one component, or two or more components.

Further, the substance which inhibits inflammation promoted by GM3 may be isolated and purified from natural products, or may be synthesized. The term "synthesized substance" includes a compound of a substance existing in nature (a derivative thereof) and a compound of a substance which has not been confirmed in nature.

In view of exerting the effect of the present invention, the substance which inhibits inflammation promoted by GM3 is preferably a glycosphingolipid in which a glycan is glycosidically linked to ceramide, and more preferably a glycosphingolipid in which the glycan has two or more of sialic acids.

Further, the substance which inhibits inflammation promoted by GM3 may be a derivative of the glycosphingolipid which has the same effect as that of the glycosphingolipid.

Further, the substance which inhibits inflammation promoted by GM3 is preferably a ganglioside having 2 or more of sialic acids in view of exerting the effect of the present invention and being safe.

In view of exerting the effect of the present invention and being safe, the ganglioside having 2 or more of sialic acids is preferably at least one ganglioside selected from the group consisting of GD1c, GD1a, GT1a, GD3, GD2, GD1b, GT1b, GQ1b, GT3, GT2, GT1c, GQ1c and GP1c, more preferably at least one ganglioside selected from the group consisting of GD1a, GD3, GD1b, GT1b and GQ1b, and particularly preferably at least one ganglioside selected from the group consisting of GD1b, GT1b and GQ1b. FIG. 1 illustrates a schematic diagram of these gangliosides.

These gangliosides may be used singly or in combination of two or more kinds thereof.

Further, the substance which inhibits inflammation promoted by GM3 is preferably GM3 having a structure represented by the following formula (1):

[Chemical Formula 3]

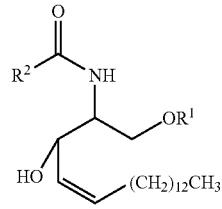

(1)

[In the formula (1), $R^1$ represents a glycan constituting ganglioside GM3, $R^2$—C(=O)— represents a fatty acid residue having 18 or less of carbon atoms, or an unsaturated fatty acid residue having 20 or more of carbon atoms.]

The GM3 having the structure represented by the formula (1) is preferably, in view of exerting the effect of the present invention and being safe, GM3 in which the fatty acid is a hydrocarbon group having 16 to 18 carbon atoms, or GM3 in which the fatty acid is a hydrocarbon group having 20 or more of carbon atoms and one double bond is included in the hydrocarbon group.

From the same point of view, it is preferable to use GM3 in which the carbon number of the fatty acid residue is 16 or 18, or GM3 in which the carbon number of the unsaturated fatty acid residue is 24 and one double bond is included in the hydrocarbon group of the unsaturated fatty acid residue.

The agent for inhibiting inflammation promoted by GM3 of the present invention may contain "other ingredients" in addition to the substance which inhibits inflammation promoted by GM3, i.e., an active ingredient.

The "other ingredients" in the agent for inhibiting inflammation promoted by GM3 are not particularly limited, and may be appropriately selected according to the purpose within the range that does not impair the effect of the present invention. Examples thereof include pharmaceutically acceptable carriers.

The carriers are not particularly limited and may be appropriately selected according to, for example, the dosage form to be described later. Further, the content of the "other ingredients" in the agent for inhibiting inflammation promoted by GM3 is not particularly limited and may be appropriately selected according to the purpose.

The dosage form of the agent for inhibiting inflammation promoted by GM3 of the present invention is not particularly limited and may be appropriately selected according to, for example, the desired administration method to be described later.

Specific examples of the dosage form include oral solid preparations (such as tablets, coated tablets, granules, powders, and capsules), oral liquid preparations (such as internal liquid preparations, syrups, and elixirs), injections (such as solvents and suspensions), ointments, patches, gels, creams, external powders, sprays, and inhalation sprays.

The oral solid preparation can be produced by, for example, adding an excipient, if necessary, additives (such as a binder, a disintegrating agent, a lubricant, a coloring agent, and a flavoring and odor-masking agent) to the active ingredient, by the ordinary method.

Examples of the excipient include lactose, saccharose, sodium chloride, dextrose, starch, calcium carbonate, kaolin, microcrystalline cellulose, and silicic acid.

Examples of the binder include water, ethanol, propanol, simple syrup, dextrose solution, starch solution, gelatin solution, carboxymethylcellulose, hydroxypropylcellulose, hydroxypropylstarch, methylcellulose, ethylcellulose, shellac, calcium phosphate, and polyvinylpyrrolidone.

Examples of the disintegrating agent include dry starch, sodium alginate, agar powder, sodium hydrogen carbonate, calcium carbonate, sodium lauryl sulfate, monoglyceride stearate, and lactose.

Examples of the lubricant include purified talc, stearate, borax, and polyethylene glycol.

Examples of the coloring agent include titanium oxide and iron oxide.

Examples of the flavoring and odor-masking agent include saccharose, orange peel, citric acid, and tartaric acid.

The oral liquid preparation can be produced by, for example, adding additives (such as a flavoring and odor-masking agent, a buffer, and a stabilizer) to the active ingredient, by the ordinary method.

Examples of the flavoring and odor-masking agent include saccharose, orange peel, citric acid, and tartaric acid. Examples of the buffer include sodium citrate. Examples of the stabilizer include tragacanth, gum arabic, and gelatin.

The injection for subcutaneous, intramuscular or intravenous administration can be produced by, for example, adding a pH adjuster, a buffer, a stabilizer, an isotonizing agent, a local anesthetic, and the like to the active ingredient.

Examples of the pH adjuster and the buffer include sodium citrate, sodium acetate, and sodium phosphate. Examples of the stabilizer include sodium pyrosulfite, EDTA, thioglycolic acid, and thiolactic acid. Examples of the isotonizing agent include sodium chloride and dextrose. Examples of the local anesthetic include procaine hydrochloride and lidocaine hydrochloride.

The content of the substance which inhibits inflammation promoted by GM3 (i.e., the active ingredient in the agent for inhibiting inflammation promoted by GM3 of the present invention) in the agent for inhibiting inflammation promoted by GM3 is not particularly limited, and it can be appropriately selected according to the purpose. The total amount of the substance which inhibits inflammation promoted by GM3 is preferably from 0.001 to 100 parts by mass, more preferably from 0.01 to 99 parts by mass, particularly preferably from 0.1 to 95 parts by mass, and further preferably from 1 to 90 parts by mass, based on 100 parts by mass of the agent for inhibiting inflammation promoted by GM3.

The animal to be administered with the agent for inhibiting inflammation promoted by GM3 of the present invention is not particularly limited, and examples thereof include humans, mice, rats, monkeys, horses, livestock such as cows, pigs, goat, chickens; and pets such as cats and dogs.

Further, the method of administering the agent for inhibiting inflammation promoted by GM3 is not particularly limited, and for example, it can be appropriately selected according to the dosage form of the agent for inhibiting inflammation promoted by GM3. Examples thereof include oral administration, intraperitoneal administration, injection into the blood, and injection into the intestine.

Further, the dosage of the agent for inhibiting inflammation promoted by GM3 is not particularly limited, and it can be selected appropriately according to the age and body weight of the individual to be administered and the degree of desired effect. For example, as for the daily dosage for adults, the amount of the active ingredient is preferably from 1 mg to 30 g, more preferably from 10 mg to 10 g, and particularly preferably from 100 mg to 3 g.

Furthermore, the timing of administration of the agent for inhibiting inflammation promoted by GM3 is not particularly limited, and it can be selected appropriately according to the purpose. For example, the agent may be administered prophylactically or therapeutically.

<Agent for Inhibiting Production of Inflammatory Cytokine>

The agent for inhibiting production of an inflammatory cytokine of the present invention comprises a substance which inhibits the production of an inflammatory cytokine promoted by GM3 as an active ingredient.

The substance which inhibits the production of an inflammatory cytokine promoted by GM3 is preferably a ganglioside having two or more of sialic acids in view of exerting the effect of the present invention and being safe.

The ganglioside having two or more of sialic acids is preferably, in view of exerting the effect of the present invention and being safe, at least one kind of ganglioside selected from the group consisting of GD1c, GD1a, GT1a, GD3, GD2, GD1b, GT1b, GQ1b, GT3, GT2, GT1c, GQ1c, and GP1c, more preferably at least one kind of ganglioside selected from the group consisting of GD1a, GD3, GD1b, GT1b, and GQ1b, and particularly preferably at least one kind of ganglioside selected from the group consisting of GD1b, GT1b, and GQ1b.

These gangliosides may be used singly or in combination of two or more kinds thereof.

Further, the substance which inhibits inflammation promoted by GM3 is preferably GM3 having a structure represented by the following formula (1):

[Chemical Formula 4]

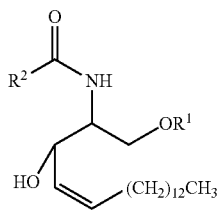

(1)

[In the formula (1), $R^1$ represents a glycan constituting ganglioside GM3, $R^2$—C(=O)— represents a fatty acid residue having 18 or less of carbon atoms, or an unsaturated fatty acid residue having 20 or more of carbon atoms.]

The GM3 having the structure represented by the formula (1) is preferably, in view of exerting the effect of the present invention and being safe, GM3 in which the carbon number of the fatty acid is from 16 to 18, or GM3 in which the carbon number of the fatty acid is 20 or more and one double bond is included in the hydrocarbon group.

From the same point of view, it is preferable to use GM3 in which the carbon number of the fatty acid residue is 16 or 18, or GM3 in which the carbon number of the unsaturated fatty acid residue is 24 and one double bond is included in the hydrocarbon group of the unsaturated fatty acid residue.

Similarly to the agent for inhibiting inflammation promoted by GM3, the agent for inhibiting production of an inflammatory cytokine of the present invention may contain "other ingredients" in addition to the active ingredient within the range that does not impair the effect of the present invention.

Further, the dosage form thereof is not particularly limited and can be appropriately selected according to, for example, the desired administration method as described above.

<Method of Inhibiting or Treating Inflammation>

Another embodiment of the present invention relates to "a method of inhibiting or treating inflammation". The method of inhibiting or treating inflammation is a method which inhibits and treats inflammation promoted by GM3 and comprises a step of administering a glycosphingolipid in which "the glycan having two or more of sialic acids" is glycosidically linked to ceramide to increase the blood concentration of the glycosphingolipid.

Further, as long as the same effect as that of the glycosphingolipid is produced, a derivative of the glycosphingolipid may be administered.

Further, the method of inhibiting or treating inflammation is a method which inhibits and treats inflammation promoted by GM3 and comprises a step of administering a ganglioside having two or more of sialic acids to increase the blood concentration of the ganglioside.

In the method of inhibiting or treating inflammation, in view of exerting the effect of the present invention, the ganglioside having 2 or more of sialic acids is preferably at least one kind of ganglioside selected from the group consisting of GD1c, GD1a, GT1a, GD3, GD2, GD1b, GT1b, GQ1b, GT3, GT2, GT1c, GQ1c, and GP1c, more preferably at least one kind of ganglioside selected from the group consisting of GD1a, GD3, GD1b, GT1b, and GQ1b, and particularly preferably at least one kind of ganglioside selected from the group consisting of GD1b, GT1b and GQ1b.

These gangliosides may be used singly or in combination of two or more kinds thereof.

Further, the method of inhibiting or treating inflammation is a method which inhibits and treats inflammation promoted by GM3 and comprises a step of administering a ganglioside having a structure represented by the following formula (1) to increase the blood concentration of the ganglioside having the structure represented by the formula (1).

Further, as long as the same effect as that of the ganglioside having the structure represented by the formula (1) is given, a derivative of the ganglioside having the structure represented by the formula (1) may be administered.

[Chemical Formula 5]

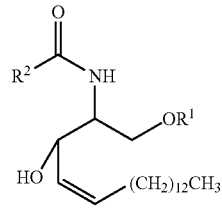

(1)

[In the formula (1), $R^1$ represents a glycan constituting ganglioside GM3, $R^2$—C(=O)— represents a fatty acid residue having 18 or less of carbon atoms, or an unsaturated fatty acid residue having 20 or more of carbon atoms.]

The GM3 having the structure represented by the formula (1) is preferably, in view of exerting the effect of the present invention and being safe, GM3 in which the fatty acid is a hydrocarbon group having 16 to 18 carbon atoms, or GM3 in which the fatty acid is a hydrocarbon group having 20 or more of carbon atoms and one double bond is included in the hydrocarbon group.

From the same point of view, it is preferable to use GM3 in which the carbon number of the fatty acid residue is 16 or 18, or GM3 in which the carbon number of the unsaturated fatty acid residue is 24 and one double bond is included in the hydrocarbon group of the unsaturated fatty acid residue.

Further, the method of inhibiting or treating inflammation is a method which inhibits and treats inflammation promoted by GM3 and comprises a step of administering the agent for inhibiting inflammation promoted by GM3 to increase the blood concentration of the agent for inhibiting inflammation promoted by GM3.

In the method of inhibiting or treating inflammation, the procedure of administering the glycosphingolipid, the ganglioside, or the agent for inhibiting inflammation promoted by GM3 may be appropriately selected according to the purpose. Examples thereof include administration by injection, oral administration, intraperitoneal administration, and enteral administration.

The dosage of the glycosphingolipid (the ganglioside or the agent for inhibiting inflammation promoted by GM3) may be appropriately selected in consideration of the symptoms, age, sex, dosage form, administration method, number of administrations per day, and the like.

EXAMPLES

Hereinafter, the present invention will be described more specifically with reference to examples, but the present invention is not limited to these examples unless the gist thereof is exceeded. "%" in the examples indicates "% by mass" unless otherwise noted.

Example 1

[Inhibitory Action of Serum Ganglioside Other than GM3 on Inflammation]

Table 1 shows the composition of gangliosides in human serum based on Non-Patent Literature 3. The human serum mainly contains GM3, and further contains GD3, GM2, GD1a, GD1b, GT1b, and "a complex ganglioside such as GQ1b" in this order.

A serum ganglioside mimic resembling the composition of these gangliosides was used to treat a macrophage-like cultured cell line in which the serum in the medium was removed and reduced: RAW 264.7 cells (0.5% fetal bovine-derived serum). Then, an actual influence on TNF-α production by TLR4 ligand (LPS) stimulation was examined.

RAW 264.7 cells cultured overnight in DMEM containing 0.5% fetal bovine serum were co-stimulated by 0.5 ng/mL of lipopolysaccharide (LPS) and glycosphingolipid (serum ganglioside mimic) at a concentration resembling the composition of serum ganglioside. 18 hours later, the TNF-α in the culture supernatant was quantitated by an ELISA method.

TABLE 1

| Species | Conc. [μM] |
| --- | --- |
| GM3 | 5.0 |
| GD3 | 1.25 |
| GM2 | 0.6 |
| GD1a | 0.375 |
| GD1b | 0.125 |
| GT1b | 0.17 |
| >GQ1b | 0.05 |
| Total | ~7.6 μM |

FIG. 2 shows the results of the ELISA method. In FIG. 2, the left column shows control, the middle column shows the result of adding LPS to the medium, and the right column shows the result of adding LPS and serum ganglioside mimic to the medium. As the numerical value on the vertical axis increases, inflammation due to macrophage activity is promoted.

It was found that the serum ganglioside mimic treatment almost completely inhibited TNF-α production from macrophages by LPS. This result suggests that the composition of gangliosides in the serum is to inhibit inadvertent activation of macrophage cells (mainly monocytes, and the like) in the circulating blood.

In addition, the influence on TNF-α production by each of gangliosides (LacCer, GM3, GM1, GD1a, GD1b, GT1b, GQ1b, and GD3) in the serum was evaluated.

RAW 264.7 cells cultured overnight in DMEM containing 0.5% fetal bovine serum were co-stimulated by LPS (0.5 ng/mL) and each glycosphingolipid (1.0 μM). 18 hours later, the TNF-α in the culture supernatant was quantitated by the ELISA method.

The results are shown in FIG. 3. In FIG. 3, the leftmost column shows the control, and the second column from the left shows the result of adding only LPS to the medium.

Surprisingly, it was found that treatment with only GM3 significantly increased TNF-α production by LPS.

On the other hand, serum ganglioside molecular species other than GM3 exhibited an action of strongly inhibiting TNF-α production by LPS. In LacCer and GM1, TNF-α was equivalent to that of the result of adding only LPS.

GD1a, GD1b, GT1b, GQ1b and GD3, which had two or more of sialic acids, strongly inhibited TNF-α production by LPS. In particular, GD1b, GT1b and GQ1b significantly strongly inhibited TNF-α production by LPS.

The action of each of the serum gangliosides was observed and evaluated in an environment with reduced serum in the medium. For the first time, these results clearly defined the enhancing effect of only GM3 on inflammation and the inhibitory action of serum ganglioside other than GM3, which had not been revealed, on inflammation.

The above results strongly suggested that an undesirable inflammatory reaction of macrophages in the blood was inhibited by the coexistence of GM3 and GD3, GD1a, GD1b, GT1b, and GQ1b in the circulating blood of healthy subjects.

Example 2

[Inhibitory Actions of Various Gangliosides in RAW 264.7 Cells on Inflammation]

Next, the concentration dependence of inhibitory action of complex-type ganglioside molecular species on the production of inflammatory cytokines induced by LPS and GM3 was examined. As indicated above, mouse macrophage-like RAW 264.7 cells produce large amounts of TNF-α in response to LPS (i.e., a component derived from *Escherichia coli*) and GM3, which is increasingly expressed during obesity.

First, the concentration-dependent inhibitory activity of inhibitory ganglioside in serum on LPS-dependent TNF-α production was examined.

RAW 264.7 cells cultured overnight in DMEM containing 0.5% fetal bovine serum were co-stimulated by LPS (2.0 ng/mL) and each glycosphingolipid (0.25 to 2.0 μM). 18 hours later, the TNF-α in the culture supernatant was quantitated by the ELISA method.

The results are shown in FIG. 4. In FIG. 4, the leftmost column shows the control, and the second column from the left shows the result of adding only LPS to the medium.

It was found that the inflammation promoted by LPS was inhibited in a concentration-dependent manner by adding each of the gangliosides (GD1a, GD1b, GT1b, and GQ1b).

Further, the concentration-dependent inhibitory action of gangliosides other than GM3 in the serum on cooperative TNF-α production by LPS and GM3 was examined.

RAW 264.7 cells cultured overnight in DMEM containing 0.5% fetal bovine serum were co-stimulated by each glycosphingolipid (0.25 to 1.0 μM), LPS (0.5 ng/mL), and GM3 (5.0 μM). 18 hours later, the TNF-α in the culture supernatant was quantitated by the ELISA method.

The results are shown in FIG. 5. In FIG. 5, the leftmost column is the control and shows the result of adding only LPS to the medium, and the second column from the left shows the result of adding only LPS and GM3 to the medium.

It was found that synergistic increases in productions of TNF-α (promotion of inflammation) by GM3 and LPS were inhibited in a concentration-dependent manner by adding each of the gangliosides (GD1a, GD1b, GT1b, and GQ1b).

Further, it was found that the addition of 1 μM (GM3 ratio; 10:1) or less of complex-type gangliosides GD1a, GD1b, GT1b, GQ1b almost completely inhibited both the TNF-α productions (FIGS. 4 and 5).

As a result of comparing the inhibitory activity of complex-type gangliosides, the 50% inhibitory concentration of each of the gangliosides relative to LPS stimulation was 0.5 μM for GD1a, 0.5 μM for GD1b, 0.5 μM for GT1b, and 0.25 μM for GQ1b (FIG. 4), meanwhile, the 50% inhibitory concentration for cooperative activation of LPS and GM3 was 0.5 μM for GD1a, 0.5 μM for GD1b, 0.25 μM for GT1b, and 0.125 μM for GQ1b (FIG. 5). It was found that the ganglioside molecule having two or more of these sialic acids in its molecule had a great inhibitory activity on the cooperative activation by LPS and GM3.

These results suggests that the inhibitory activity of gangliosides other than GM3 on inflammation acts more strongly on macrophage activation induced by GM3 which is increasingly expressed during obesity. Further, it was found for the first time in this example that inflammation was inhibited at a concentration in a physiological environment or a ganglioside concentration lower than that (Table 1 and FIGS. 4 and 5).

Example 3

[Inhibitory Action of Various Gangliosides in Mouse Bone Marrow-Derived Macrophages on Inflammation]

Next, the inhibitory action of inhibitory ganglioside in serum on LPS-dependent TNF-α production in bone marrow-derived macrophages was examined.

Bone marrow-derived cells harvested from the femur and tibia of C57/BL6 mice were induced to differentiate for one week using 20 ng/mL of recombinant macrophage colony-stimulating factor (M-CSF). The obtained bone marrow-derived macrophages (BMDMs) were cultured overnight in DMEM containing 0.5% fetal bovine serum and co-stimulated with LPS (0.5 ng/mL) and each glycosphingolipid (10 μM). 18 hours later, the TNF-α in the culture supernatant was quantitated by the ELISA method.

The results are shown in FIG. 6. In FIG. 6, the leftmost column shows the control, and the second column from the left shows the result of adding only LPS to the medium.

It was found that LPS-dependent TNF-α production (promotion of inflammation) in bone marrow-derived macrophages was inhibited by adding each of the gangliosides (GD1a, GD1b, GT1b, and GQ1b).

Further, the inhibitory activity of inhibitory ganglioside in serum on cooperative TNF-α production by LPS and GM3 in bone marrow-derived macrophages was examined.

Bone marrow-derived cells harvested from the femur and tibia of C57/BL6 mice were induced to differentiate for one week using 20 ng/mL of recombinant macrophage colony-stimulating factor (M-CSF). The obtained bone marrow-derived macrophages (BMDMs) were cultured overnight in DMEM containing 0.5% fetal bovine serum and co-stimulated with LPS (0.5 ng/mL), GM3 (10 μM), and each glycosphingolipid (10 μM). After 18 hours, the TNF-α in the culture supernatant was quantified by the ELISA method.

The results are shown in FIG. 7. In FIG. 7, the leftmost column is the control and shows the result of adding only LPS only to the medium, and the second column from the left shows the result of adding only LPS and GM3 to the medium.

It was found that "cooperative TNF-α production (promotion of inflammation) by LPS and GM3" in bone marrow-derived macrophages was strongly inhibited by adding each of the gangliosides (GD1a, GD1b, GT1b, and GQ1b) (FIG. 7).

Further, comparison of FIG. 6 to FIG. 7 suggests that the inhibitory activity of each of the gangliosides (GD1a, GD1b, GT1b, and GQ1b) on inflammation is more strongly exerted on macrophage activation induced by GM3 which is increasingly expressed during obesity.

Example 4

[Formulation of Agent for Inhibiting Inflammation Promoted by GM3]

«Tablet»

20.0 mg of GD1b, 40 mg of lactose, 20 mg of starch, and 5 mg of low-substituted hydroxypropylcellulose were uniformly mixed, and then the resultant mixture was subjected to a wet granulation method using 8% by mass of an aqueous solution of hydroxypropyl methylcellulose as a binder, thereby producing granules for tableting. 0.5 mg to 1.5 mg of the magnesium stearate required to impart lubricity to the granules for tableting was added, and then the mixture was tableted using a tableting machine to form tablets.

«Liquid Preparation»

10.0 mg of GT1b was dissolved in 10 mL of 2% by mass of 2-hydroxypropyl-β-cyclodextrin aqueous solution to form a liquid preparation for injection.

Example 5

[Enhancing or Inhibitory Action of Various Gangliosides in Humans on Inflammation]

Human peripheral blood-derived monocytes (CD14 positive cells) were cultured in DMEM (Low Glucose) containing 0.5% FCS and 25 ng/mL of granulocyte/macrophage colony stimulating factor, and co-stimulated with 0.125 ng/mL of E. coli-derived lipopolysaccharide (LPS, E. coli O111:B4), and 1.25, 2.5, or 5.0 μM of N-mix (neutral glycosphingolipid mixture (Glc-Cer, Lac-Cer, Gb3, and Gb4)) or each of the ganglioside molecular species. 18 hours later, the inflammatory cytokines (IL-6, IL-1β, and TNF-α) secreted in the culture supernatant were quantitated using the ELISA method. The results are shown in FIGS. 8 to 10.

In FIGS. 8 to 10, the leftmost column shows the control, and the second column from the left shows the result of adding only LPS to the medium.

Regarding the structure of each of the GM3 species, for example, "GM3C16" indicates that the fatty acid of GM3 is a hydrocarbon group having 16 carbon atoms. Further, "GM3hC24" indicates that the fatty acid of GM3 is a hydrocarbon group having 24 carbon atoms and the fatty acid has an OH group as a substituent. Furthermore, "GM3C24:1" indicates that the fatty acid of GM3 is a hydrocarbon group having 24 carbon atoms and one double bond is included in the hydrocarbon group.

As a result of FIGS. 8 to 10, it was surprisingly found that "GM3C16", "GM3C18" and "GM3C24:1" among the GM3 molecular species exhibited the action of inhibiting the production of IL-6, IL-1β and TNF-α by LPS.

On the other hand, among GM3 molecular species, "GM3C22" and "GM3C24", in which the fatty acid had no OH group and no double bond was included in the hydrocarbon group, and "GM3hC24" in which the fatty acid had an OH group, significantly enhanced the production of IL-6, IL-1p, and TNF-α by LPS.

Example 6

[Inhibitory Action of GM3C16, GM3C18, and GM3C24:1 in Humans on Inflammation]

Next, it was examined whether in response of promotion of TLR4-selective inflammatory cytokine production caused by "GM3C22" and "GM3C24", in which the fatty acid had no OH group and no double bond was included in the hydrocarbon group, among the GM3 molecular species, "GM3C16", "GM3C18", and "GM3C24:1", in which a double bond was included in the hydrocarbon group, exhibited an antagonistic inhibitory action on inflammation in human monocytes.

Under the same culture conditions as in Example 5, "GM3C16", "GM3C18" or "GM3C24:1" which inhibited inflammation was combined to "GM3C22" or "GM3C24" which promoted inflammation. The resultant combination was added to the monocytes and further stimulated with 0.06 ng/mL of LPS (i.e., a TLR4 activating factor). 18 hours later, the inflammatory cytokine IL-6 secreted in the culture supernatant was quantitated using the ELISA method. The results are shown in FIG. 11.

In the results of FIG. 11, "GM3C16", "GM3C18", and "GM3C24:1" strongly inhibited production of IL-6 in response to not only LPS stimulation but also stimulation promoted by the addition of "GM3C22" and "GM3C24". Interestingly, "GM3C16", "GM3C18", and "GM3C24:1" strongly inhibited production of IL-6 during TLR4 activation promoted by the addition of "GM3C22" and "GM3C24", compared to TLR4 activation by only LPS.

Example 7

[Toll-Like Receptor Selective Enhancing and Inhibitory Action of GM3 on Inflammation]

Inflammation associated with activation of human monocytes is known to be caused by activation of Toll-like receptor (TLR) on human monocytes. In addition to LPS which is an activating factor for TLR4, there are other various activating factors for TLR.

Then, under the same culture conditions as in Example 5, human monocytes were stimulated using any of 0.125 ng/mL of LPS (i.e., TLR4 activating factor), 5.0 μg/mL of high mobility group box 1 (HMGB 1) (i.e., a TLR4 and TLR2 activating factors), 20 ng/mL of Pam3Csk4 (i.e., a TLR1 and TLR2 activating factors), 1.0 ng/mL of MALP-2 (i.e., TLR2 and TLR6 activating factors), 50 ng/mL of Flagellin (i.e., a TLR5 activating factor), and 250 ng/mL of R-848 (i.e., TLR7 and TLR8 activating factors); and 5 μM of GM3 molecular species. 18 hours later, the inflammatory cytokine IL-6 secreted in the culture supernatant was quantitated using the ELISA method. The results are shown in FIGS. 12A and B.

In the results of FIGS. 12A and B, among the GM3 molecular species, "GM3C22" and "GM3C24", in which the fatty acid had no OH group and no double bond was included in the hydrocarbon group, and "GM3hC24", in which the fatty acid had an OH group, selectively increased IL-6 production by LPS and HMGB1 (i.e., factors activating TLR4). On the other hand, no increase in IL-6 production was observed in other TLR activating factors.

Furthermore, among the GM3 molecular species, "GM3C16", "GM3C18", and "GM3C24:1" exhibited an inhibitory action on IL-6 production by LPS and HMGB1 (i.e., factors activating TLR4) (FIG. 12A). This inhibitory action was also observed in IL-6 production by Pam3Csk4 (i.e., a factor activating TLR2), but the inhibitory action on IL-6 production by LPS and HMGB1 (i.e., factors activating TLR4) was more significant.

Summary of Examples

Focusing on the composition of gangliosides in human serum, GD1a, GD1b, and GT1b (approximately 0.5 to 1.0 μM) are reported to be contained in the most dominant GM3 (5 μM) (Table 1). From this, it is considered that activation of innate immune cells by LPS is very strongly inhibited in human blood containing GM3 and a complex of ganglioside.

Further, GD1b, GT1b, and GQ1b, which have been very strongly inhibiting TNF-α production by LPS in the Examples, are common in that they are biosynthesized from GD3 in mammals (FIG. 1).

Many innate immune cells that circulate in the blood are activated only after reaching infected tissues and target organs, causing an immune response. On the other hand, inadvertent innate immune activation in the blood is considered to be one of the factors causing systemic immune dysfunction represented by septic shock, chronic inflammatory diseases and the like. Gangliosides in the blood are thought to have a role of preventing innate immune cells in the circulation from being activated. These gangliosides are artificially administered, whereby uncontrollable chronic inflammatory diseases and systemic inflammatory conditions can be more effectively dealt with.

Although it is confirmed that specific gangliosides such as GD3, GD1a, GD1b, GT1b, and GQ1b inhibit macrophage activation by LPS of GM3, it is possible to inhibit GM3-dependent macrophage activation by saturated fatty acids (palmitic acid), pathogen-associated molecular patterns (PAMPs), damage-associated molecular patterns (DAMPs) except for LPS.

In particular, it is revealed that, in human monocytes, "GM3C16", "GM3C18", and "GM3C24:1" have an inhibitory activity on inflammation (FIGS. 8 to 10) and more strongly inhibit TLR4 activation promoted by GM3 molecular species such as "GM3C22" and "GM3C24", compared to TLR4 activation by only LPS (FIG. 11). Further, it is revealed that GM3 molecular species selectively act on TLR4, thereby promoting inflammation and inhibiting inflammation (FIGS. 12A and B).

From these results, the inflammation inhibitor based on the GM3 structure has characteristics which can selectively and strongly inhibit TLR4 activation caused by sepsis, chronic inflammation, metabolic syndrome, and the like, and TLR4 activation promoted by GM3. Furthermore, the inflammation inhibitor also has revolutionary characteristics in which the inhibitor hardly causes side effects such as immunodeficiency associated with the inhibition of the whole immune system, which is significantly observed in known immunosuppressants, because it is difficult to inhibit the activation of other TLRs.

FIG. 13 illustrates the mechanism in which LPS-dependent inflammation is enhanced or inhibited by ganglioside molecular species, as expected from the results of this example.

"GM3C24" and "GM3hC24" act directly or indirectly on the TLR4/MD2 complex, thereby enhancing NF-κB activation by binding of the TLR4/MD2 complex and promoting production of inflammatory cytokines (IL-6, IL-1p, and TNF-α).

On the other hand, it is considered that "GM3C16", "GM3C18", and "GM3C24:1" inhibit the NF-κB activation by directly or indirectly acting on the TLR4/MD2 complex or other TLRs (Toll-like receptor), and inhibits the production of inflammatory cytokines (IL-6, IL-1β, and TNF-α).

Further, gangliosides having two or more of sialic acids (such as GD1a, GD1b, GT1b, GQ1b, and GD3) directly or indirectly act on Siglecs (i.e., sialic acid-binding immunoglobulin-like lectin), thereby inhibiting the NF-κB activation and inhibiting the production of inflammatory cytokines (IL-6, IL-1β, and TNF-α).

INDUSTRIAL APPLICABILITY

The agent for inhibiting inflammation promoted by GM3 of the present invention inhibits inflammation promoted by GM3, is safe, and is expected to exert an effect on chronic inflammatory diseases, systemic inflammatory conditions, and the like. Therefore, the agent can be widely used in the pharmaceutical field, medical field, and the like.

This application is based on Japanese Patent Application No. 2015-232564 filed on Nov. 30, 2015 and Japanese Patent Application No. 2016-114188 filed on Jun. 8, 2016, and the contents of all of these applications are incorporated herein by reference and incorporated as disclosure of the specification of the present invention.

The invention claimed is:

1. A method of inhibiting or treating chronic inflammation in a subject during obesity promoted by GM3, comprising a step of administering to the subject a substance which inhibits the chronic inflammation during obesity promoted by GM3, as an active ingredient, to increase the blood concentration of the substance, wherein a daily dosage of the active ingredient is 1 mg to 30 g, and wherein the substance is GD1a or a ganglioside having a structure represented by the following formula (1):

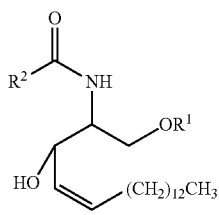

(1)

in the formula (1), $R^1$ represents a glycan constituting ganglioside GM3, $R^2$—C(═O)— represents a fatty acid residue having 18 or less of carbon atoms, or an unsaturated fatty acid residue having 20 or more of carbon atoms.

2. The method according to claim 1, wherein the substance is the ganglioside having the structure represented by the formula (1).

3. A method of inhibiting production of an inflammatory cytokine which induces chronic inflammation in a subject during obesity promoted by GM3, comprising a step of administering to the subject a substance which inhibits the production of the inflammatory cytokine promoted by GM3 as an active ingredient, to increase the blood concentration of the substance, wherein a daily dosage of the active ingredient is 1 mg to 30 g, and wherein the substance is GD1a or a ganglioside having a structure represented by the following formula (1):

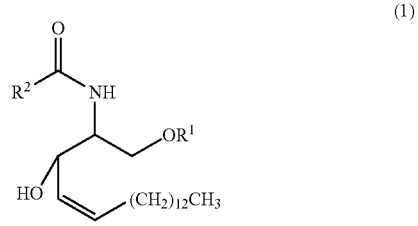

(1)

in the formula (1), $R^1$ represents a glycan constituting ganglioside GM3, $R^2$—C(═O)— represents a fatty acid residue having 18 or less of carbon atoms, or an unsaturated fatty acid residue having 20 or more of carbon atoms.

4. The method according to claim 3, wherein the substance is the ganglioside having the structure represented by the formula (1).

* * * * *